(12) United States Patent
Speier et al.

(10) Patent No.: US 11,478,159 B2
(45) Date of Patent: Oct. 25, 2022

(54) INFLOW-BASED PULSE WAVE VELOCITY PROFILING ALONG THE AORTA USING MAGNETIC RESONANCE IMAGING

(71) Applicant: Siemens Healthcare GmbH, Erlangen (DE)

(72) Inventors: Peter Speier, Erlangen (DE); Kelvin Chow, Chicago, IL (US); Ning Jin, Powell, OH (US)

(73) Assignee: Siemens Healthcare GmbH, Erlangen (DE)

( * ) Notice: Subject to any disclaimer, the term of this patent is extended or adjusted under 35 U.S.C. 154(b) by 1186 days.

(21) Appl. No.: 15/828,900

(22) Filed: Dec. 1, 2017

(65) Prior Publication Data

US 2019/0167125 A1   Jun. 6, 2019

(51) Int. Cl.
*A61B 5/021* (2006.01)
*G06T 7/00* (2017.01)
*G06T 1/00* (2006.01)
*A61B 5/055* (2006.01)
*G06T 11/00* (2006.01)
*G01R 33/563* (2006.01)
(Continued)

(52) U.S. Cl.
CPC ........ *A61B 5/02125* (2013.01); *A61B 5/0263* (2013.01); *A61B 5/02116* (2013.01); *A61B 5/055* (2013.01); *A61B 5/7285* (2013.01); *G01R 33/56325* (2013.01); *G06T 1/0007* (2013.01); *G06T 7/00* (2013.01); *G06T 11/003* (2013.01); *G16H 30/40* (2018.01); *A61B 2576/02* (2013.01); *G01R 33/4835* (2013.01); *G06T 2207/10088* (2013.01)

(58) Field of Classification Search
None
See application file for complete search history.

(56) References Cited

U.S. PATENT DOCUMENTS 6,141,578 A * 10/2000 Hardy ................. A61B 5/0285
                                                    324/306
2011/0234222 A1 * 9/2011 Frahm ................ G01R 33/4824
                                                    324/309

OTHER PUBLICATIONS

Wentland AL, Grist TM, Wieben O. Review of MRI-based measurements of pulse wave velocity: a biomarker of arterial stiffness. Cardiovasc Diagn Ther. Apr. 2014;4(2): 193-206. (Year: 2014).*

(Continued)

*Primary Examiner* — Luther Behringer
(74) *Attorney, Agent, or Firm* — Banner & Witcoff Ltd.

(57) ABSTRACT

In a method and magnetic resonance (MR) apparatus for pulse wave velocity (PWV) measurement along the aorta of a subject using MR imaging, a multislice cardio synchronized segmented ciné MR data acquisition sequence is optimized in order to enhance inflow representation in the slice images, in order to make the multislice MR data acquisition sequence viable for clinical uses, so as to acquire intensity-based MR data from two transverse slices spaced from each other along the descending aorta. The respective intensities of relevant pixels in at least two respective slice images are analyzed in order to identify the arrival of a pulse wave in the respective slices by the onset of flow enhancement in the slices, represented by intensity changes in the pixels. From the onset of flow enhancement in the respective slice images, PWV is calculated. An electronic signal representing the calculated PWV is then provided from a computer.

23 Claims, 6 Drawing Sheets

(51) Int. Cl.
  *A61B 5/00*   (2006.01)
  *A61B 5/026*  (2006.01)
  *G16H 30/40*  (2018.01)
  *G01R 33/483* (2006.01)

(56) References Cited

OTHER PUBLICATIONS

Tse DHY, Wiggins CJ, Poser BA. High-resolution gradient-recalled echo imaging at 9.4T using 16-channel parallel transmit simultaneous multislice spokes excitations with slice-by-slice flip angle homogenization. Magn Reson Med. Sep. 2017;78(3):1050-1058. (Year: 2017).*

Kozerke S, Scheidegger MB, Pedersen EM, Boesiger P. Heart motion adapted cine phase-contrast flow measurements through the aortic valve. Magn Reson Med. Nov. 1999;42(5):970-8. (Year: 1999).*

Wigström L, Lindström L, Sjöqvist L, Thuomas KA, Wranne B. M-mode magnetic resonance imaging: a new modality for assessing cardiac function. Clin Physiol. Jul. 1995;15(4):397-407. (Year: 1995).*

Runge, Val M. et al. Physics of Clinical MRI Taught Through Images. Thieme. 2014. pp. 36-37. (Year: 2014).*

"Determinants of Pulse Wave Velocity in Healthy People and in the Presence of Cardiovascular Risk Factors: Establishing Normal and Reference Values," European Heart Journal, vol. 31, pp. 2338-2350 (2010).

Spronck et al. "Pressure-Dependence of Arterial Stiffness: Potential Clinical Implications," Journal of Hypertension, vol. 33, Issue 2, pp. 230-338 (2015).

Zhang et al., "Tube-Load Model Parameter Estimation for Monitoring Arterial Hemodynamics," Frontiers in Physiology, 2:72 (2011).

Wentland et al., "Review of MRI-based Measurements of Pulse Wave Velocity: A Biomarker of Arterial Stiffness," Cardiovascular Diagnosis and Therapy, vol. 4(2), pp. 193-206 (2014)(study "A").

W.H. Wallis, University of Freiburg (2012) entitled "Beslimmung der Pulswellengeschwindigkeit der Aorta mithilfe der Flusssensitiven 4D Magnetresonanztomographie" ("Determination of Pulse Wave Velocity of the Aorta With the Use of Flow-Sensitive 4D Magnetic Resonance Tomography").

Li et al., "Performance Assessment of Pulse Wave Imaging Using Conventional Ultrasound in Canine Aortas ex vivo and Normal Human Arteries in vivo," Artery Res., vol. 11, pp. 19-28 (2015).

Sugawara et al., "Distal Shift of Arterial Pressure Wave Relflection Sites with Aging," Hypertension, vol. 56, No. 5, pp. 920-925 (2010).

* cited by examiner

INFLOW-BASED PULSE WAVE VELOCITY PROFILING ALONG THE AORTA USING MAGNETIC RESONANCE IMAGING

BACKGROUND OF THE INVENTION

Field of the Invention

The present invention concerns a method and apparatus for pulse wave velocity (PWV) measurement, and in particular concerns a magnetic resonance imaging method and apparatus for PWV determination.

Description of the Prior Art

Pulse wave velocity (PWV) is the speed of propagation of a pressure change in a medium. PWV is related to the amplitude of the propagating wave, the properties of the medium in which the wave propagates (density, compressibility, sound velocity, etc.), and the boundary conditions. For example, for a straight pipe geometry, the diameter and elasticity of the pipe wall are relevant. These last-noted relevant factors are exploited for medical purposes, in order to characterize the stiffness of a vessel tree. Stiffness scales with, and thus can be used to classify, the severity of arteriosclerosis. Stiffness also increases significantly with age, and therefore the vessel stiffness is sometimes characterized by an apparent age.

The standard measurement method of PWV for medical purposes determines the time for a pulse wave to propagate from the heart to two easily accessible and separated arteries, such as the carotids and the arteria femoralis. The distance that the pulse wave must travel between the two measurement points depends on the geometry of the connecting vessels, and is estimated from the body shape of the patient in whom the measurement is being made. From such a measurement, an average PWV along the vessel tree can be derived.

The clinical distribution of PWV values for this type of measurement is summarized in "Determinants of Pulse Wave Velocity in Healthy People and in the Presence of Cardiovascular Risk Factors: Establishing Normal and Reference Values," European Heart Journal, Volume 31, pp. 2338-2350 (2010).

The average PWV in a healthy population with optimal blood pressure increases steadily with age, from about 6 m/s for age <30 years, to 10 m/s for age >70 years. For worst case blood pressure (Grade II/III HT), average values range from 8 m/s for age <30 years to 14 m/s for age >70 years. Extreme values in this study were 4 m/s and 21 m/s.

The global PWV measurement method has been validated against localized invasive pressure measurements in the large vessels. These invasive measurements, while considered as the gold standard, are not clinically practical due to the high cost and risks associated with the necessary invasive procedure.

If clinically viable localized PWV measurements were possible, such measurements could provide a direct insight into local physiological processes.

It is known that globally measured PWV varies with blood pressure. In fact, PWV can be used to track blood pressure over a short period of time. The abstract of Spronck et al. "Pressure-Dependence of Arterial Stiffness: Potential Clinical Implications," Journal of Hypertension, Volume 33, Issue 2, pp. 230-338 (2015) states "a near 1 m/s decrease in carotid PWV occurs given the roughly 10 mmHg decrease in diastolic pressure." Therefore, it can be expected that local PWV in the aorta will correlate with local pressure. A local measurement of PWV in the aorta thus would allow a PWV profile to be created from which a pressure profile along the vessel can be derived.

An important function of the elastic aorta is to take up energy of the pulse wave that occurs with the heartbeat. This elasticity will, in turn, reduce the local PWV along the aorta. This means that the variation of the PWV along the aorta is directly related to this function, and it should be possible to characterize that function from the measurement results.

In addition, there are multiple sources for PWV variations along the aorta. These include areas with increased calcification that locally increase stiffness, and variations in the aortic arch can increase the local PWV. Wall thickness variations and changes in the lumen also can affect PWV. In addition, pulse waves are reflected at patient-specific reflection sites. The interfering forward and backward proceeding waves will create local PWV and waveform variations. The pattern of superposition is physiologically relevant, and could be determined from the PWV variations.

Complex analytical models are required in order to describe the physiology of the aorta in detail, as exemplified by Zhang et al., "Tube-Load Model Parameter Estimation for Monitoring Arterial Hemodynamics," Frontiers in Physiology, 2:72 (2011). In addition to heuristically-found parameters to describe the state and function of the aorta, a localized PWV measurement can provide input parameters for these models.

Therefore, a need exists for a high quality, non-invasive local PWV measurement technique, which enables PWV profiling in a clinically acceptable time.

In general terms, magnetic resonance imaging (MRI) has been proposed for implementing PWV measurements. A review of methods for MRI-based PWV measurements is provided in Wentland et al., "Review of MRI-based Measurements of Pulse Wave Velocity: A Biomarker of Arterial Stiffness," Cardiovascular Diagnosis and Therapy, Volume 4(2), pp. 193-206 (2014)(study "A").

All such conventional MRI-based methods rely on characterizing the local velocity by phase contrast imaging. Velocity over the duration of a cardiac cycle is measured at two or more positions in the aorta, typically covering both the ascending and descending aorta in one image slice. PWV is then calculated from the transit time required for the wave to travel from the ascending to the descending aorta. Typically, the onset of the pulse is detected from the baseline intersection of a straight line fitted to the rising flank of the pulse wave. Because these two vessels are connected by the short aortic arch, the transit time is quite short (approximately 10 ms), and must be comparable to the time resolution of the measurement, which is typically 2 to 5 times larger. Thus, in these conventional methods, time interpolation based on the wave shape is crucial. Alternative methods use 4D flow data sets, as described in the doctoral thesis of W. H. Wallis, University of Freiburg (2012) entitled "Bestimmung der Pulswellengeschwindigkeit der Aorta mithilfe der Fluss-sensitiven 4D Magnetresonanztomographie" ("Determination of Pulse Wave Velocity of the Aorta With the Use of Flow-Sensitive 4D Magnetic Resonance Tomography"). Other alternative methods place the aorta inside the detected slice, and measure inplane flow in order to determine the pulse travel time along the aorta. Again, the flow is detected by phase contrast, and while the number of data points has increased, the time resolution is still very low compared to the resolution required for clinically meaningful results.

In order to be clinically relevant, the required accuracy and precision of a PWV measurement should be at least sensitive enough to differentiate the changes that occur in a healthy population of patients, namely to differentiate age groups in 10 year bins, or in one of five blood pressure categories of study "A". This suggests a required precision of 10%. Since magnetic resonance measures transit time, which is inversely proportional to PWV, this precision is harder to achieve for high values of PWV, than for lower values.

Selecting a realistic transit gap d=200 mm and PWV=10 m/s as a "normal" value in older patients results in a transit time dt=d/PWV=20 ms. In order to achieve the aforementioned 10% precision, a time resolution, for determining the onset of the pulse wave, below 2 ms is required.

SUMMARY OF THE INVENTION

An object of the present invention is to provide a non-invasive, clinically viable procedure for localized PWV measurements, which allow local physiological processes derived from said measurements.

The above object is achieved in accordance with the present invention by a method for PWV measurement along the aorta of a subject wherein an MR data acquisition scanner is operated, while a subject is situated therein, in order to acquire intensity-based magnetic resonance (MR) data respectively from two transverse slices that are spaced from each other along the descending aorta, by executing a multi-slice MR data segmented ciné acquisition sequence (i.e. a multi-phase measurement with the acquisition spread out over multiple heartbeats, wherein the number of lines of data in k-space in each heartbeat is considered a "segment") in which nuclear spins in the respective slices are excited with a flip angle and with a repetition time (TR). The acquisition is synchronized to the cardiac motion and covers, with high temporal resolution, the relevant initial part of the cardiac cycle during which the pulse wave initial slope travels through the measured slices. The acquired multislice MR data are provided to a reconstruction computer, which reconstructs an MR slice image of each slice. Each MR slice image is composed of pixels, which each have an intensity value in the respective MR slice image. The MR slice images are provided to an analysis computer or processor, which detects the arrival of a pulse wave in each of at least two of the slices from onset flow enhancement based on the intensity values of relevant pixels derived respectively from at least two of the MR slice images. The analysis processor or computer calculates PWV from the identified arrival of the pulse wave in the two slices, and provides an electronic signal as an output therefrom, which represents the calculated PWV.

The aforementioned relevant pixels constitute the cross-cut of the same vessel under investigation, typically the aorta in the simultaneously or interleaved measured slices. The relevant pixels can be determined by an input made by an operator, by outlining a region of interest (ROI), or by automated image analysis. The ROI in an image is converted into an intensity value by averaging over the pixel intensities inside the ROI.

The multi-slice MR data acquisition sequence is preferably a simultaneous multi-slice (SMS) MR data acquisition sequence, but it is also possible to acquire multiple slices that are interleaved with each other, with the slices being non-simultaneously acquired. The slices are not interleaved geometrically, but the data collection jumps between slices, i.e., line 1 of slice 1, line 1 of slice 2, line 2 of slice 1, line 2 of slice 2, etc.

The spacing between the slices along the aorta may be between 100 mm and 400 mm. The slices may have an in-plane resolution in a range between 4 mm and 10 mm. The flip angle may be 30° and the TR is approximately 3 ms, possibly as low as 2 ms.

A preferred sequence for inflow enhancement is the GRE SMS 2 segmented ciné sequence (GRE=gradient recalled echo, SMS=simultaneous multi-slice), optimized to have the aforementioned flip angle of approximately 30° and a short TR of approximately 3 ms, for strong in-slice saturation. The flip angle is limited by specific absorption rate (SAR) requirements, and by the need for a signal to be present downstream in the slice. The slices are oriented approximately transversely so as to cut approximately perpendicularly through the descending aorta in two slice that are approximately 10 mm thick. As noted above, the slice distance is between 100 and 400 mm.

The present invention also encompasses an MR imaging apparatus having a control computer that operates an MR data acquisition scanner of the apparatus, in order to implement the method as described above.

The present invention also encompasses a non-transitory, computer-readable data storage medium encoded with programming instructions that, when the storage medium is loaded into a computer or computer system of an MR imaging apparatus, cause the computer or computer system to operate the MR data acquisition scanner in order to implement the method as described above.

DESCRIPTION OF THE PREFERRED EMBODIMENTS

Figure 1:
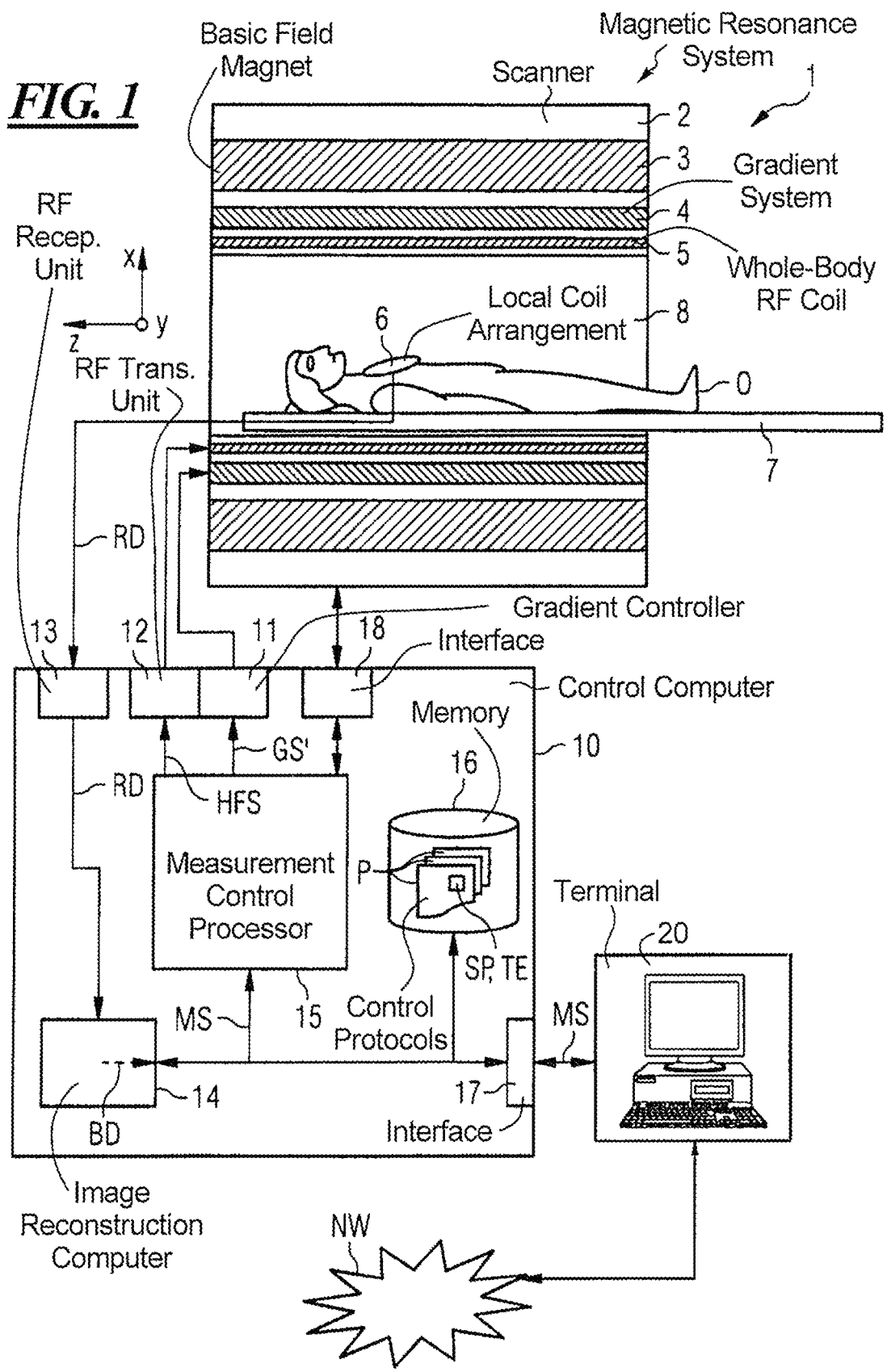
FIG. 1 schematically illustrates a magnetic resonance (MR) apparatus constructed and operating in accordance with the present invention.

A magnetic resonance system 1 according to the invention is schematically shown in FIG. 1. It includes the actual magnetic resonance scanner 2 with an examination space or patient tunnel located therein. A bed 7 can be driven into this patient tunnel 8, such that a patient O or examination subject lying on the bed 7 can be supported at a defined position within the magnetic resonance scanner 2 relative to the magnet system and radio-frequency system arranged therein during an examination, or can be moved between different positions during a measurement.

Basic components of the magnetic resonance scanner 2 are a basic field magnet 3, a gradient system 4 with magnetic field gradient coils to generate magnetic field gradients in the x-, y- and z-directions, and a whole-body radio-frequency (RF) antenna 5. The magnetic field gradient coils can be controlled independently of one another in the x-, y- and z-directions so that gradients can be applied in arbitrary logical spatial directions (for example in the slice-selection direction, in the phase coding direction or in the readout direction) via a predetermined combination, wherein these directions normally depend on the selected slice orientation. The transmission (radiation) of RF signals in order to induce of magnetic resonance signals in the examination subject O can take place via the whole-body antenna 5. The MR signals are received with a local coil 6, which can be composed of one or more individual reception coils. The local coil 6 can also be used to radiate the RF signals. All of these components are known in principle to those skilled in the art and therefore are only schematically shown in FIG. 1.

The components of the magnetic resonance scanner 2 are controlled by a control computer, which can be formed by a number of individual computers (which may be spatially separated and connected among one another via suitable cables or the like). This control computer 10 is connected via a terminal interface 17 with a terminal 20 via which an operator can control the entire system 1. In the present case, this terminal 20 (as a computer) is equipped with keyboard, one or more monitors and additional input devices (for example mouse or the like) so that a graphical user interface is provided to the operator.

Among other things, the control computer 10 has a gradient controller 11 that can in turn have multiple sub-components. Via this gradient controller 11, the individual gradient coils are provided with control signals according to a gradient pulse sequence GS. These gradient pulses are radiated (activated) at precisely provided time positions and with a precisely predetermined time curve during a measurement.

The control computer 10 also has a radio-frequency transmission unit 12 in order to feed electrical signals respectively representing radio-frequency pulses into the whole-body radio-frequency coil 5 (or the local coil 6) according to a predetermined radio-frequency pulse sequence RFS of the pulse sequence MS. The radio-frequency pulse sequence RFS includes excitation and/or refocusing pulses. The reception of the magnetic resonance signals then occurs with the use of the reception coils of the local coil 6, and the raw data RF received in this manner are read out and processed by an RF reception unit 13. The magnetic resonance signals are passed in digital form as raw data RF to a reconstruction computer 14, which reconstructs the image data BD from the raw data using the reconstruction algorithm described above, and stores the image data BD in a memory 16 and/or passes the image data BD via the interface 17 to the terminal 20 so that the operator can view the image. The image data BD can also be stored at other locations via a network NW and/or be displayed and evaluated.

Control commands are transmitted via an interface 18 to other components of the magnetic resonance scanner 2 (such as the bed 7 or the basic field magnet 3, for example), and measurement values or other information are received.

The gradient controller 11, the RF transmission unit 12 and the RF reception unit 13 are controlled, in a coordinated manner, by a measurement control processor 15. Via corresponding commands, this ensures that the desired gradient pulse sequences GS and radio-frequency pulse sequences RFS are emitted. Moreover, for this purpose it must be ensured that the magnetic resonance signals are read out by the reception coils of the local coil array 6 by the RF reception unit 13 at the appropriate point in time and are processed further. The measurement control processor 15 likewise controls the interface 18.

The basic operation of such a magnetic resonance measurement (apart from the reconstruction described above) and the cited components to control it are known to those skilled in the art, so that they need not be described in further in detail herein. Moreover, such a magnetic resonance scanner 2 and the associated control device can have an additional components that are likewise not explained in detail herein. It should also be noted that the magnetic resonance scanner 2 can also be designed differently—for example with a laterally open patient space, or as a smaller scanner in which only one body part is positioned.

In order to start a measurement, via the terminal an operator can typically select a control protocol P provided for this measurement from a memory 16 in which a number of control protocols P for different measurements are stored. Among other things, this control protocol P includes various control parameters for the respective measurement. Among these control parameters are specific basic rules for the desired pulse sequence, for example whether it is a spin echo sequence, a turbo spin echo sequence, etc. These control parameters also designated the magnetizations of nuclear spins to be achieved via the individual radio-frequency pulses, rules about the k-space trajectory to be used to enter the raw data into k-space, as well as parameters that set slice thicknesses, slice intervals, number of slices, echo time in a spin echo sequence, etc.

With the use of the terminal 20, the operator can modify a portion of these control parameters in order to create an individual control protocol for a currently desired measurement. For this purpose, variable control parameters are offered for modification at a graphical user interface of the terminal, for example.

Moreover, via a network NW the operator can retrieve control protocols (for example from a manufacturer of the magnetic resonance system 1) and may possibly modify such protocols, in order to operate the system.

Figure 2:
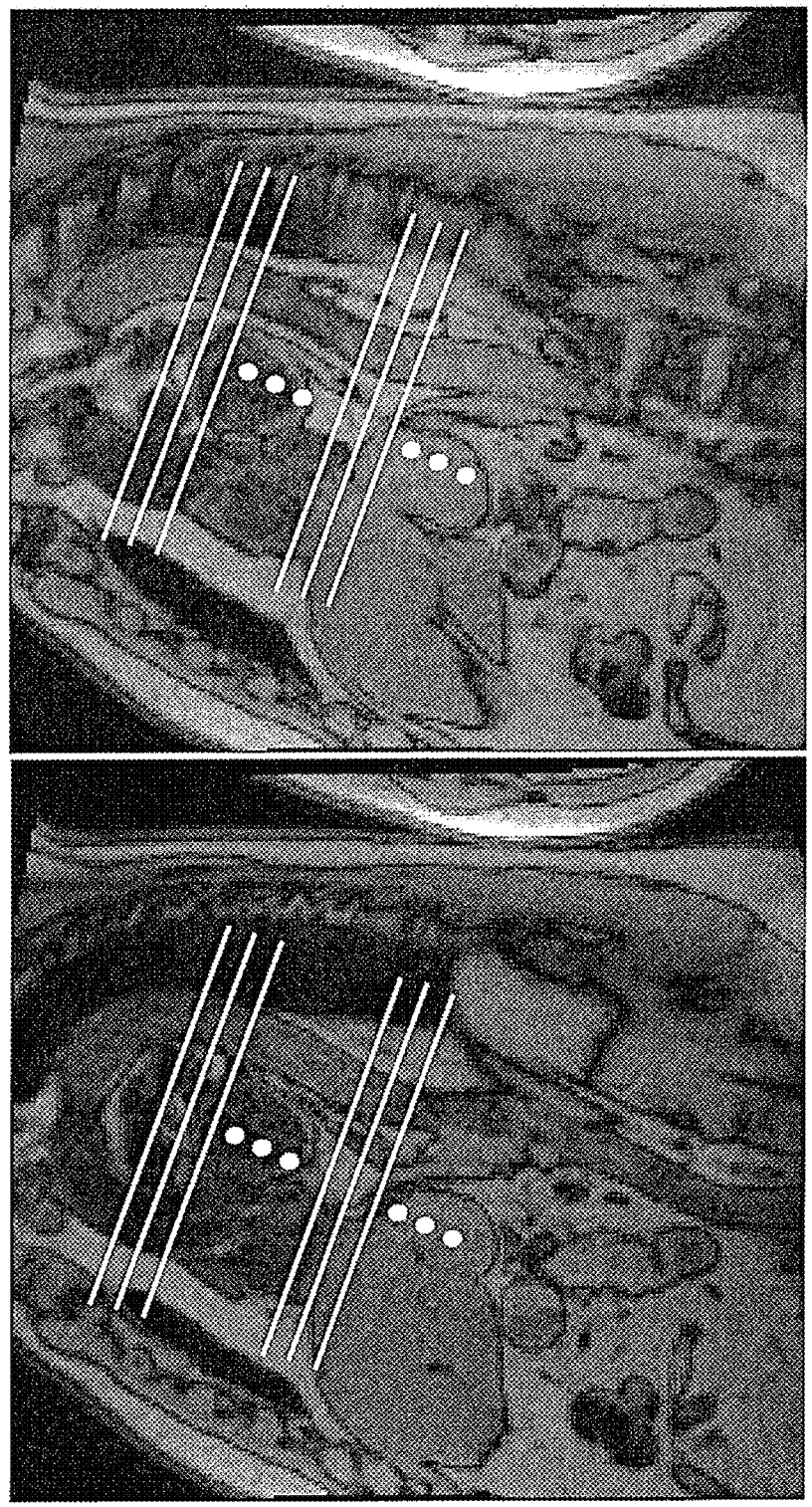
FIG. 2 shows examples of slice planning for an embodiment of the method according to the invention using an SMS MR imaging sequence and schematic designations of the same slices with ROIs covering the ascending aorta in the proximal slice group and the descending aorta in both slice groups.
Figure 6:
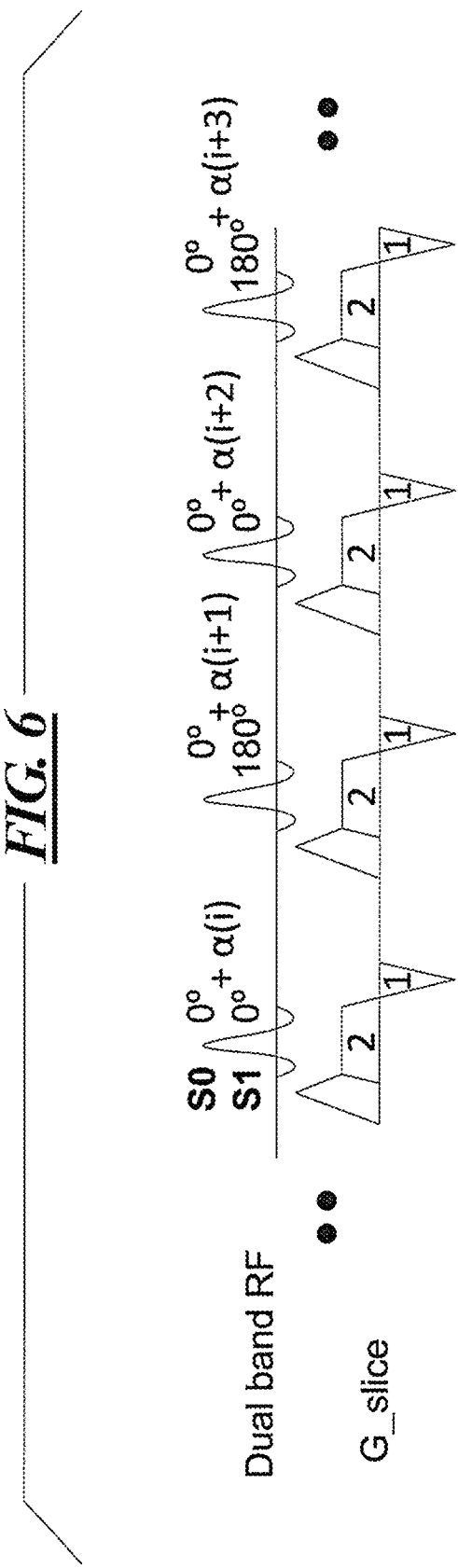
FIG. 6 is a pulse diagram of the GRE SMS 2 sequence.

In accordance with the invention, a measurement sequence for inflow enhancement, preferably an SMS sequence such as the GRE SMS 2 sequence shown in FIG. 6, is optimized in order to make use of such a measurement sequence for making a clinically viable PWV measurement. This optimization involves designing the RF excitation or refocusing pulses of the sequence so as have a high flip angle of approximately 30°, and a short repetition time (TR) of approximately 3 ms, for strong in-slice saturation. The flip angle is limited by SAR requirements, and by the need for a detectable signal to still be present in the slice downstream. The spacing between, an orientation of, the slices can be as shown in the example of FIG. 2, wherein a slice pair is oriented approximately transversely, so as to cut through the descending aorta approximately perpendicularly, into slice that are approximately 10 mm thick, and with a spacing between the slices in a range between 100 mm and 400 mm.

Further in accordance with the invention, the spatial resolution is selected as low as possible, in order to reduce the scan time while maximizing the time resolution. In the slice images produced in accordance with the present invention, there is no need to be able to separate all anatomical structures, but only to be able to see or detect contrast changes over the cardiac cycle, which indicate the arrival of the pulse wave. These changes occur inside the great vessels, which may also show respiratory motion, especially close to the interior surface, but not in the neighborhood of the aorta. Therefore, the imaging resolution need only be good enough so as to be able to separate vessels with different pulsation behavior, i.e., arteries and veins or the ascending and descending aorta. Therefore, an in-plane resolution on the order of 4-10 mm is sufficient.

Also in accordance with the invention, the time resolution is further increased by using partial phase and readout Fourier, because the measurement is intensity-based rather than phase-based. The acquired raw data can be entered into k-space asymmetrically.

The MR data acquisition in accordance with the invention is decoupled from any breath hold requirement, so as to further increase the temporal resolution. Therefore, the data acquisition in accordance with the invention is conducted with free breathing, over several respiratory cycles, such as for 30 s. The data acquisition can repeated multiple times, with the results of each individual measurement then being averaged. In this manner, resolutions of 1-3 segments of 2.5 to 10 ms are possible (compared to 30 to 40 ms for PC 2D breath-held measurement). It should be noted that the IPAT (integrated parallel acquisition techniques) function or option appears to introduce additional noise into such a free-breathing scenario, possibly due to the g-factor or due to data inconsistency, and therefore it is preferable not to activate that feature or option during the measurement that is made in accordance with the invention.

Figure 3:
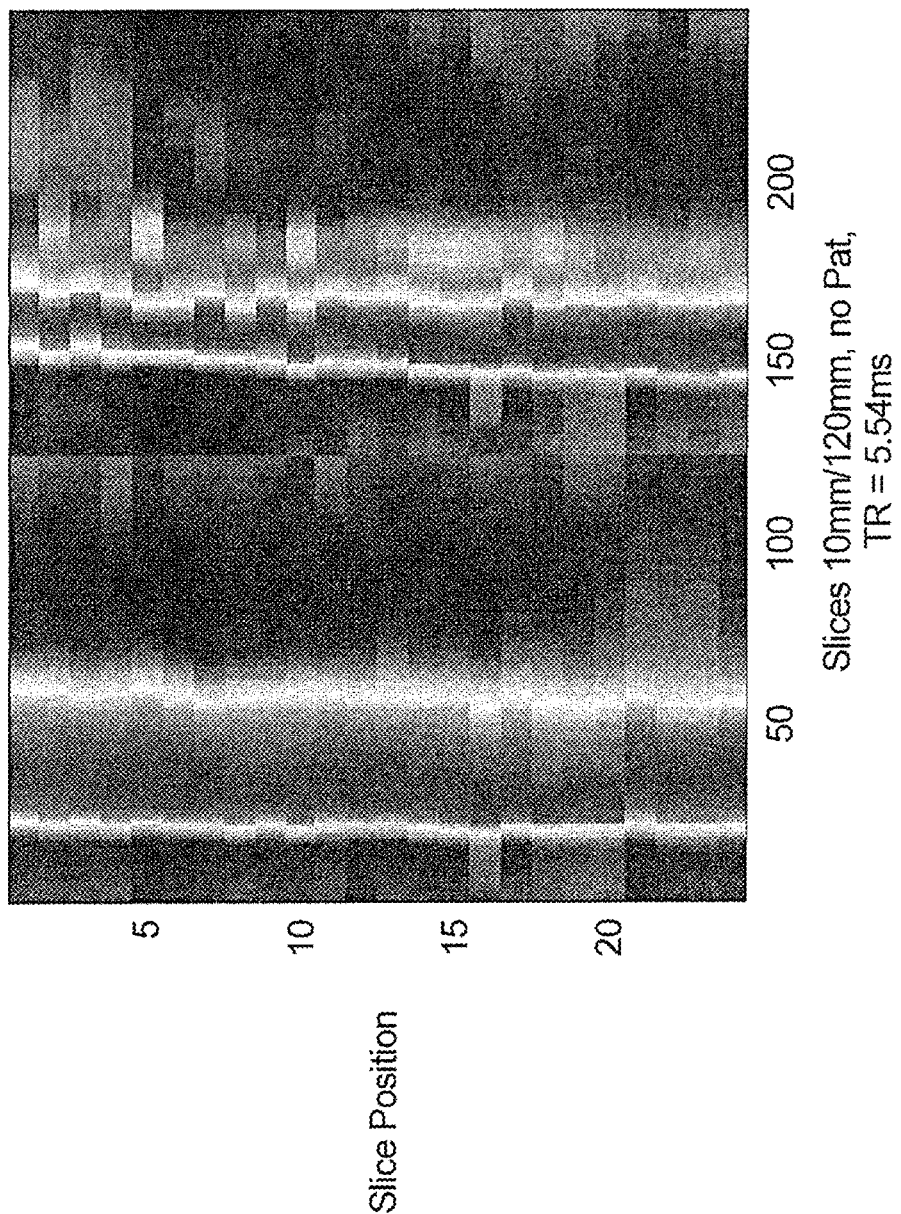
FIG. 3 shows two displays of intensity curves during the cardiac cycle (horizontal axis) for different slice positions (vertical axis) obtained in accordance with the invention, wherein the left half shows the curve for the proximal slice of the simultaneously or interleaved acquired slice pair, and the right half shows the curves for the distal slices of the pair.
Figure 4:
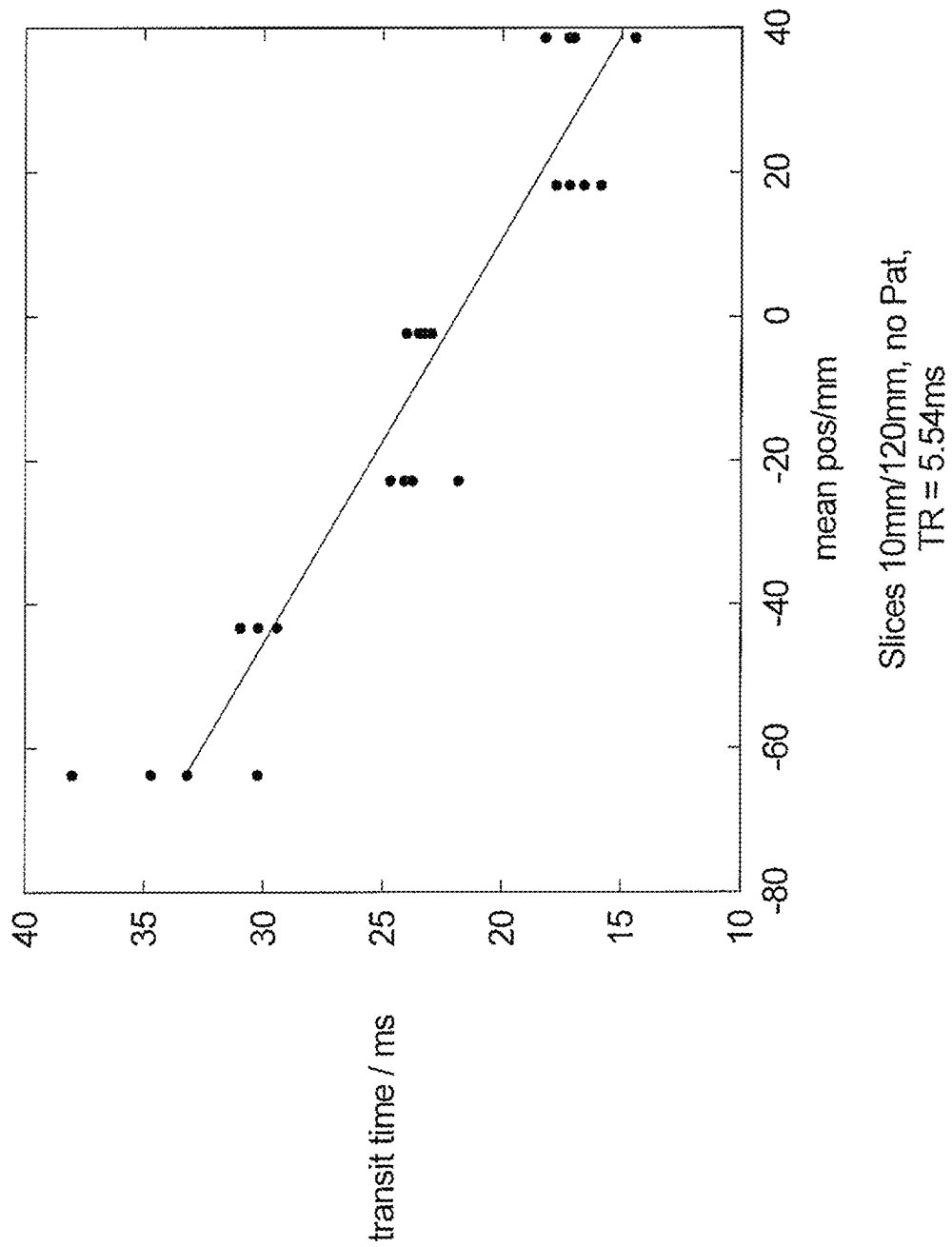
FIG. 4 shows an example of a PWV profile obtained in accordance with the present invention.
Figure 5:
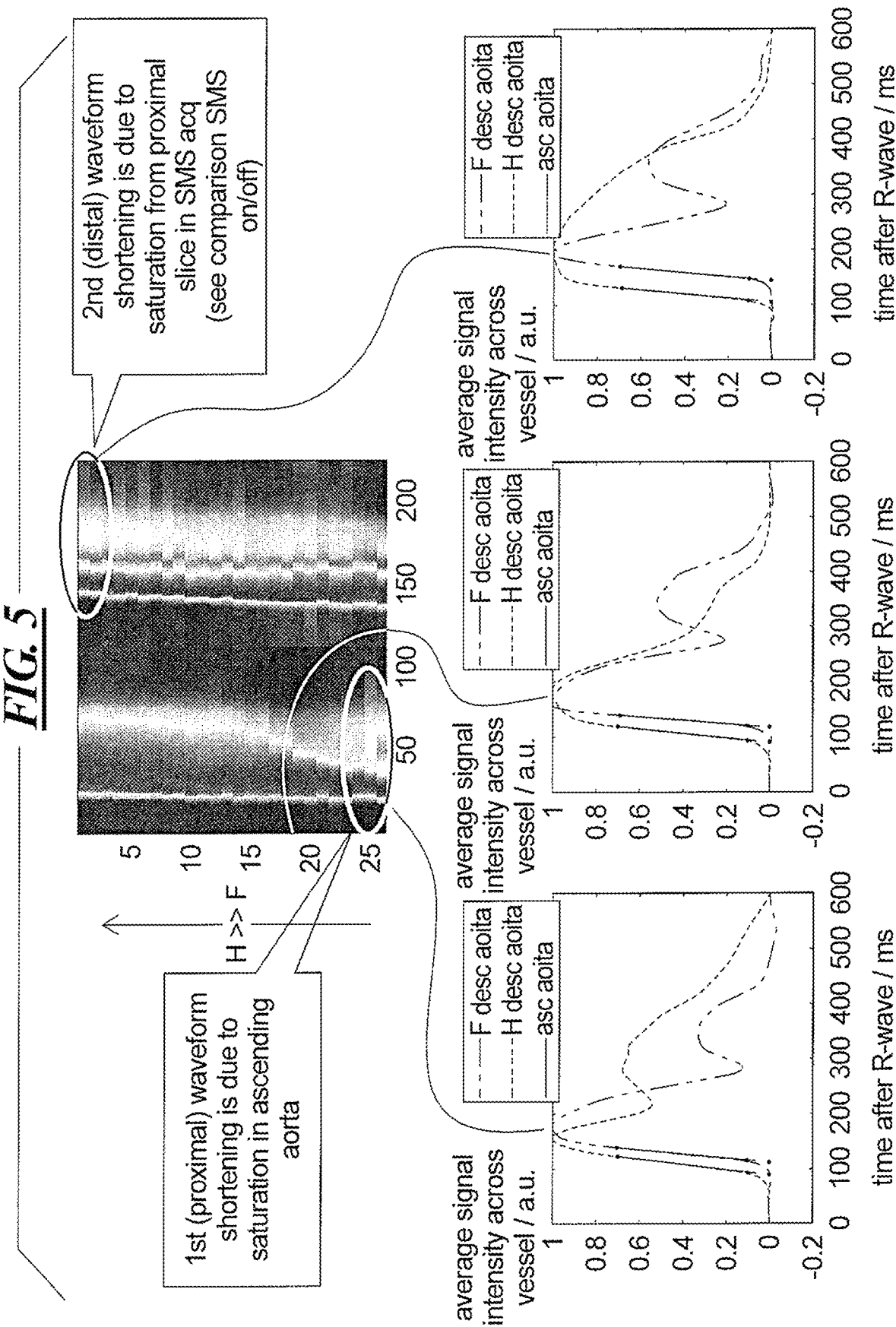
FIG. 5 schematically illustrates an example of inflow saturation from proximal slices, in accordance with the present invention.

The acquired slice images are then analyzed in order to detect the arrival of PWV from the onset of inflow enhancement. The onset of the signal increase is estimated using any of the known rising flank-based methods, using a signal that is averaged over the vessel lumen. Alternative methods based on the entire waveform, or on the maximum position, are not reliable for evaluation of inflow-based SMS measurements, because the slice upstream saturates the spins in the slice downstream, and saturation levels change when the pulse wave traverses the slice, and the transmit time of spins from the proximal slice to the distal slice changes. This can be seen FIGS. 3 and 4, showing the effect of measurements related to transit time and slice position. FIG. 5 shows the effect of inflow saturation from proximal slices.

It is optionally possible to additionally obtain a profile of the PWV along the aorta. Because the method described herein is rapid, and is not limited to breathholds (i.e., the method can be implemented with a free-breathing subject), it can be repeated under different conditions, such as for varying heart frequencies, blood pressure levels during exercise, etc. The effects of each of these changes can be measured in detail based on a PWV profile. Preferably, the measurements are repeated for different positions along the descending aorta, in order to generate such a PWV profile.

Further additional options are to determine, from the PWV profile, average or localized aortic wall characteristics. Such aortic wall characteristics may be, for example, wall stiffness, elasticity, and the characterization of the physiological Windkessel effect of the aorta. Results can be presented on a scale as a representation of the average apparent age of the aorta. Further analysis can be used in order to determine other characteristics, such as the position and the physiological effect of effective reflection sites, as described in Sugawara et al., "Distal Shift of Arterial Pressure Wave Reflection with Aging Hypertension," Hypertension, Vol 56(5), pp. 920-925 (2010).

In accordance with the present invention, it can be seen for the first time that a consistent PWV decrease occurs when moving away from the heart along the descending aorta. The only indication in the literature with regard to this effect is a small curvature that can be seen in FIGS. 1d and 1f in an article by Ronny et al., "Performance Assessment of Pulse Wave Imaging Using Conventional Ultrasound in Canine Aortas Ex Vivo and Normal Human Arteries In Vivo," Artery Res., Vol. 11, pp. 19-28 (2015), which is not analyzed in that article.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for pulse wave velocity (PWV) measurement along the aorta of a subject, using magnetic resonance (MR) imaging, said method comprising:
using a control computer to operate an MR data acquisition scanner, while a subject is situated in the scanner, in order to acquire intensity-based MR data respectively from at least two transverse slices spaced from each other along the descending aorta, by executing a multislice cardio synchronized segmented ciné MR data acquisition sequence;
using a reconstruction computer to reconstruct MR slice images, composed of pixels, of each of said at least two slices from the MR data acquired therefrom with said sequence, each of said pixels exhibiting an intensity value in said MR slice images;
providing said MR slice images to an analysis computer and using said analysis computer to detect arrival of a pulse wave respectively in different slices from onset flow enhancement based on intensity values of relevant pixels derived respectively from at least two of said MR slice images;
in said analysis computer, calculating PWV from said arrival of said pulse wave respectively in said at least two of said MR slice images, wherein the calculation lacks reliance on a local velocity measured by phase contrast imaging; and
providing an electronic output from the analysis computer that represents the calculated PWV.

2. A method as claimed in claim 1 comprising operating said MR data acquisition scanner to execute said multislice cardio synchronized segmented ciné MR data acquisition sequence as a simultaneous multi-slice MR data acquisition sequence.

3. A method as claimed in claim 2 comprising using a GRE SMS 2 sequence as said simultaneous multi-slice cardio synchronized segmented ciné MR data acquisition sequence.

4. A method as claimed in claim 1 comprising operating said MR data acquisition scanner to execute said multi-slice cardio synchronized segmented ciné MR data acquisition sequence with multiple slices being acquired interleaved.

5. A method as claimed in claim 1 comprising operating said MR data acquisition scanner to execute said multi-slice cardio synchronized segmented ciné MR data acquisition sequence over multiple respiratory cycles of the subject.

6. A method as claimed in claim 5 comprising operating said MR data acquisition scanner to execute said multi-slice cardio synchronized segmented ciné MR data acquisition sequence over said multiple respiratory cycles of the subject while the subject is freely breathing.

7. A method as claimed in claim 1 comprising operating said MR data acquisition scanner to repeat said multi-slice cardio synchronized segmented ciné MR data acquisition sequence multiple times in order to acquire slice images along respectively different positions of the descending aorta in the respective repetitions, and, from the MR slices obtained at said different positions in said multiple repetitions, generating a PWV profile in the descending aorta.

8. A method as claimed in claim 1 comprising using a PWV profile in said analysis computer to identify at least one of local vessel stiffness of the subject, windpipe function of the subject, reflection sites in the subject, and an apparent age of vessels in the subject.

9. A method as claimed in claim 1 comprising acquiring said intensity-based MR data from at least two transverse slices that are spaced from each other along the descending aorta in a spacing range between 100 mm and 400 mm.

10. A method as claimed in claim 1 comprising operating said MR data acquisition scanner to excite nuclear spins in the respective at least two transverse slices by radiating a radio frequency pulse with a flip angle of approximately 30°.

11. A method as claimed in claim 1 comprising operating said MR data acquisition scanner to excite nuclear spins in the respective at least two transverse slices, and to acquire said intensity-based MR data respectively from said at least two transverse slices, with a repetition time that is less than or equal to 2 ms.

12. A magnetic resonance (MR) apparatus for pulse wave velocity (PWV) measurement along the aorta of a subject using MR imaging, said MR apparatus comprising:
an MR data acquisition scanner;
a control computer configured to operate said MR data acquisition scanner, while a subject is situated in the scanner, in order to acquire intensity-based MR data respectively from at least two transverse slices spaced from each other along the descending aorta, by executing a multislice cardio synchronized segmented ciné MR data acquisition sequence;
a reconstruction computer configured to reconstruct an MR slice image, composed of pixels, of each of said at least two slices from the MR data acquired therefrom with said sequence, each of said pixels exhibiting an intensity value in respective MR slice images;
an analysis computer provided with said MR images, said analysis computer being configured to detect arrival of a pulse wave respectively in different slices from onset flow enhancement based on intensity values of relevant pixels derived respectively from at least two of said MR slice images;
said analysis computer being configured to calculate PWV from said arrival of said pulse wave respectively in said at least two of said MR slice images, wherein the calculation lacks reliance on a local velocity measured by phase contrast imaging; and
said analysis computer being configured to provide an electronic output from the analysis computer that represents the calculated PWV.

13. An MR apparatus as claimed in claim 12 wherein said control computer is configured to operate said MR data acquisition scanner to execute said multislice cardio synchronized segmented ciné MR data acquisition sequence as a simultaneous multi-slice MR data acquisition sequence.

14. An MR apparatus as claimed in claim 13 wherein said control computer is configured to use a GRE SMS 2 sequence as said simultaneous multi-slice cardio synchronized segmented ciné MR data acquisition sequence.

15. An MR apparatus as claimed in claim 12 wherein said control computer is configured to operate said MR data acquisition scanner to execute said multi-slice cardio synchronized segmented ciné MR data acquisition sequence with multiple slices being acquired interleaved.

16. An MR apparatus as claimed in claim 12 wherein said control computer is configured to operate said MR data acquisition scanner to execute said multi-slice cardio synchronized segmented ciné MR data acquisition sequence over multiple respiratory cycles of the subject.

17. An MR apparatus as claimed in claim 12 wherein said control computer is configured to operate said MR data acquisition scanner to execute said multi-slice cardio synchronized segmented ciné MR data acquisition sequence over said multiple respiratory cycles of the subject while the subject is freely breathing.

18. An MR apparatus as claimed in claim 12 wherein said control computer is configured to operate said MR data acquisition scanner in order to repeat said multi-slice MR cardio synchronized segmented ciné MR data acquisition sequence so as to acquire slice images along respectively different positions of the descending aorta in the respective petitions, and, from the MR slices obtained at said different positions, generating a PWV profile in the descending aorta.

19. An MR apparatus as claimed in claim 18 comprising using said PWV profile in said analysis computer to identify at least one of local vessel stiffness of the subject, windpipe function of the subject, reflection sites in the subject, and an apparent age of vessels in the subject.

20. An MR apparatus as claimed in claim 12 comprising acquiring said intensity-based MR data from at least two transfer slices that are spaced from each other along the descending aorta in a spacing range between 100 mm and 400 mm.

21. An MR apparatus as claimed in claim 12 comprising operating said MR data acquisition scanner to excite nuclear spins in the respective at least two transverse slices by radiating a radio frequency pulse with a flip angle of approximately 30°.

22. An MR apparatus as claimed in claim 12 comprising operating said MR data acquisition scanner to excite nuclear spins in the respective at least two transverse slices, and to acquire said intensity-based MR data respectively from said at least two transverse slices, with a repetition time that is less than or equal to 2 ms.

23. A non-transitory, computer-readable data storage medium encoded with programming instructions, said storage medium being loaded into a computer system of a magnetic resonance (MR) apparatus that comprises an MR data acquisition scanner, and said programming instructions causing said computer system to:
operate the MR data acquisition scanner, while a subject is situated in the scanner, in order to acquire intensity-based MR data respectively from at least two transverse slices spaced from each other along the descending aorta, by executing a multislice cardio synchronized segmented ciné MR data acquisition sequence;
reconstruct an MR slice image, composed of pixels, of each of said at least two slices from the MR data acquired therefrom with said sequence, each of said pixels exhibiting an intensity value in respective MR slice images;
detect arrival of a pulse wave respectively in different slices from onset flow enhancement based on intensity values of relevant pixels derived respectively from at least two of said MR slice images;

calculate pulse wave velocity (PWV) from said arrival of said pulse wave respectively in said at least two of said MR slice images, wherein the calculation lacks reliance on a local velocity measured by phase contrast imaging; and provide an electronic output from the computer system that represents the calculated PWV.

* * * * *